(12) United States Patent
Hess et al.

(10) Patent No.: US 6,740,102 B2
(45) Date of Patent: May 25, 2004

(54) VESSEL HARVESTING RETRACTOR WITH BILATERAL ELECTROSURGICAL LIGATION

(75) Inventors: Christopher J. Hess, Lebanon, OH (US); Michael F. Clem, Maineville, OH (US); Gary W. Knight, West Chester, OH (US); Kristin L. Jambor, Cincinnati, OH (US); Gary L. Long, Mariemont, OH (US)

(73) Assignee: Ethicon, Inc., Somerville, NJ (US)

( * ) Notice: Subject to any disclaimer, the term of this patent is extended or adjusted under 35 U.S.C. 154(b) by 60 days.

(21) Appl. No.: 09/967,205

(22) Filed: Sep. 28, 2001

(65) Prior Publication Data

US 2003/0065349 A1 Apr. 3, 2003

(51) Int. Cl.⁷ .............................. A61B 1/32; A61B 1/00; A61B 17/00; A61B 17/22

(52) U.S. Cl. .................. 606/159; 600/210; 600/235; 600/114; 606/190

(58) Field of Search ................. 600/105, 104, 600/210, 212; 606/192, 159, 170

(56) References Cited

U.S. PATENT DOCUMENTS

| | | | |
|---|---|---|---|
| 5,667,480 A | 9/1997 | Knight et al. | |
| 5,695,514 A | * 12/1997 | Chin | 606/190 |
| 5,722,934 A | 3/1998 | Knight et al. | |
| 5,725,479 A | 3/1998 | Knight et al. | |
| 5,759,150 A | 6/1998 | Konou et al. | |
| 5,817,013 A | 10/1998 | Ginn et al. | |
| 5,891,140 A | 4/1999 | Ginn et al. | |
| 5,913,818 A | 6/1999 | Co et al. | |
| 5,916,233 A | 6/1999 | Chin | |
| 5,921,919 A | 7/1999 | Chin et al. | |
| 5,970,982 A | * 10/1999 | Perkins | 128/898 |
| 6,019,771 A | * 2/2000 | Bennett et al. | 606/159 |
| 6,022,313 A | * 2/2000 | Ginn et al. | 600/114 |
| 6,036,713 A | * 3/2000 | Kieturakis | 606/190 |
| 6,042,538 A | * 3/2000 | Puskas | 600/114 |
| 6,053,863 A | 4/2000 | Chin et al. | |
| 6,083,223 A | 7/2000 | Baker | |
| 6,129,661 A | 10/2000 | Iafrati et al. | |
| 6,228,024 B1 | 5/2001 | Co et al. | |
| 6,277,137 B1 | 8/2001 | Chin | |
| 6,296,640 B1 | * 10/2001 | Wampler et al. | 606/48 |
| 6,319,265 B1 | * 11/2001 | Ginn | 606/159 |
| 6,520,975 B2 | * 2/2003 | Branco | 606/159 |

* cited by examiner

Primary Examiner—Michael J. Milano
Assistant Examiner—P Roberts
(74) Attorney, Agent, or Firm—Scully, Scott, Murphy & Presser

(57) ABSTRACT

A method and device for endoscopic harvesting of blood vessels from a patient for use in subsequent procedures. The device having a two piece headpiece. A vessel to be removed is inserted into the headpiece and the top and bottom portions of the headpiece are alternatively extended in reciprocating fashion to dissect above and below the vessel. The headpiece having electrodes for ligation of any side branch vessels which are uncovered in the dissection process.

19 Claims, 7 Drawing Sheets

VESSEL HARVESTING RETRACTOR WITH BILATERAL ELECTROSURGICAL LIGATION

FIELD OF THE INVENTION

This invention relates to surgical devices and methods for dissection and removal of blood vessels from a patients body. In particular this invention relates to endoscopic vessel harvesting devices and methods.

BACKGROUND OF THE INVENTION

Endoscopic harvesting of vessels is well known in the surgical field and has been the subject of a great deal of recent technological advancement. Typically, the harvesting of vessels is performed so that the vessels can be then used for procedures such as Cardio Artery Bypass Grafting (CABG). In this procedure the saphenous veins of the legs are harvested for subsequent use in the CABG surgery.

Known methods and devices for performing vessel harvesting are discussed in detail in U.S. Pat. No. 5,667,480 issued Sep. 16, 1997 and U.S. Pat. No. 5,722,934 issued Mar. 3, 1998, both issued to Knight, et al, both of which are incorporated herein by their reference.

In the traditional endoscopic harvesting devices shown in prior art FIG. 1, there is provided a hollow shaft 12 connected to a concave headpiece 16 located at the distal end of the shaft which provides a workspace 18. An endoscope 5 is typically inserted in the shaft so that the surgeon may view workspace. The leading edge of the headpiece 16 is used for dissecting the vessel from the surrounding tissue. The device may also have guides located on the underside of the device which allow for the entry of other devices such as dissectors, ligation tools, and cutting tools, into the workspace.

The traditional method for removal of a vessel section is shown in FIGS. 2 and 3. Initially an incision 3 is made and the vessel 7 is located. Then, the vessel is dissected from the surrounding tissue using the leading edge of the headpiece 16 of the device to separate the tissue from the vessel 7. At this time there is sufficient space created around the vessel 7 so that other instruments can be inserted into the incision 3 via the guides located on the underside of the device. These instruments include ligation tools for securing side branch vessels 9, vessel dissectors for performing a more complete dissection of the vessel 7 which is to be removed, and laproscopic scissors for the transection of both the side branch vessels 9 and the vessel 7 which is to be removed.

Of the know techniques for harvesting vessels and devices used for such procedures, as in the case in the above described procedure and device, the blunt dissection is performed using the headpiece 16 of the device, and then any dissection to be performed under the device must be performed using other tools which must be inserted into the patient following the original incision 3. Upon the discovery of a side branch vessel 9 still further tools must be inserted into the incision 3 for performing the ligation and transection function.

The tool exchanges of instruments, and in fact the instruments themselves complicate the procedure. They require a great deal of skill to master and no matter the skill of the person performing the procedure, the process requires a great deal of time to perform.

Accordingly, it is an object of the present invention to overcome the short comings of the prior art by providing a device which can limit the number of tools required to perform the removal of the vessel, decrease the number of tool exchanges necessary to perform the removal, and increase the efficiency and ease of operation of the entire procedure.

SUMMARY OF THE INVENTION

The present invention overcomes the limitations of the devices of the prior art by providing a means by which a user can dissect both above and below the vessel which is to be removed using only a single tool. Further, the device is capable of ligating any side branch vessels without the insertion of any extra tools.

The device of the present invention minimizes the number of tool exchanges, the total number of tools required, and increases the users efficiency.

Accordingly, a vessel harvesting device is provided. The vessel harvesting device comprises a shaft having a lumen for insertion of an endoscope therethrough. The device has a handle located on a proximate end of the shaft for allowing an operator to manipulate the device. The device is also equipped with a headpiece connected to a distal end of the shaft, the headpiece has a top and a bottom portion, these two portions define a gap that surrounds a vessel inserted therein. The two portions of the headpiece are used to dissect above and below the vessel.

The device has means for reciprocating either the top or the bottom portion relative to the other. The headpiece has a first opening for receiving a dissected portion of the vessel and one or more second openings allowing a dissected portion of a vessel to exit the headpiece. The vessel is dissected from the surrounding tissue by reciprocating one of the top and bottom portions as the headpiece is advanced along the length of the vessel.

The device may be fit with electro-surgical ligation electrodes for ligation of side branch vessels. The electrodes can be energized by an energizing means to ligate side branch vessels. The device may also be fit with a transection element. The transection element may be a raised portion of one of the upper and lower portions of the headpiece.

Also provided is a headpiece for an endoscopic vessel harvesting device. The headpiece comprises a top portion for dissecting the tissue above a vessel which is to be removed. The top portion is typically rigidly attached to the endoscopic harvesting device. The device further comprises a bottom portion for dissecting the tissue below the vessel to be removed. The bottom portion is connected to the endoscopic harvesting device by an articulated connection. The top and bottom portions define a gap into which a vessel is inserted, the top and bottom portions then surround the vessel. There is an opening in the headpiece for receiving a dissected portion of the vessel and one or more openings in the headpiece allowing a dissected portion of the vessel to exit the headpiece after dissection. The device dissects a vessel from the surrounding tissue by reciprocating the bottom portion relative to the top portion while traversing the length of the vessel.

The headpiece may be fit with electro-surgical ligation electrodes for ligation of side branch vessels. The electrodes can be energized by an energizing means to ligate side branch vessels. The headpiece may also be fit with a transection element. The transection element may be a raised portion of one of the upper and lower portions of the headpiece.

Still yet provided is a method of vessel dissection comprising a series of steps. Initially, the vessel to be harvested must be located, then an incision to expose the vessel must be made. Next, the surgeon must pre-dissect the vessel from tissue above the vessel. Then, the surgeon must pre-dissect below the vessel. Upon having a portion of the vessel dissected both above and below, a portion of the vessel which has been pre-dissected is inserted into a two piece headpiece of the vessel harvesting device so that a top and a bottom portion of the headpiece surround the vessel. Then the vessel is dissected from the tissue by projecting the top portion of the headpiece along the vessel and by simultaneously reciprocating the bottom portion of the headpiece. Dissection is accomplished by repeating the previous two steps while traversing the length of the vessel. Finally the vessel is ligated, transected and removed. When a side branch vessel is uncovered it too must be ligated and transected using the ligation and transection means of the vessel harvesting device.

DETAILED DESCRIPTION OF THE INVENTION

Figure 1:
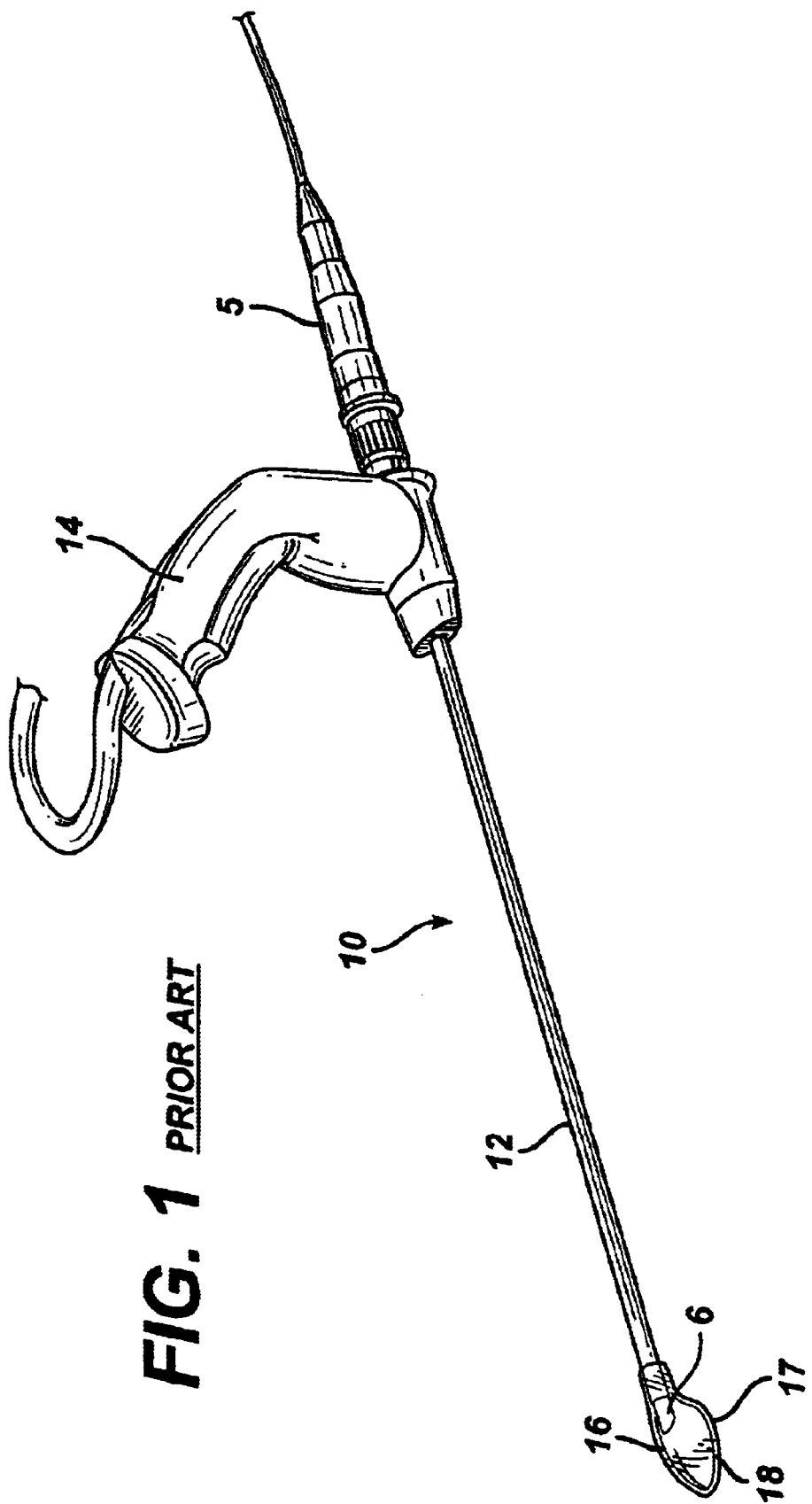
FIG. 1 illustrates a perspective view of an endoscopic vessel harvesting device of the prior art.
Figure 2:
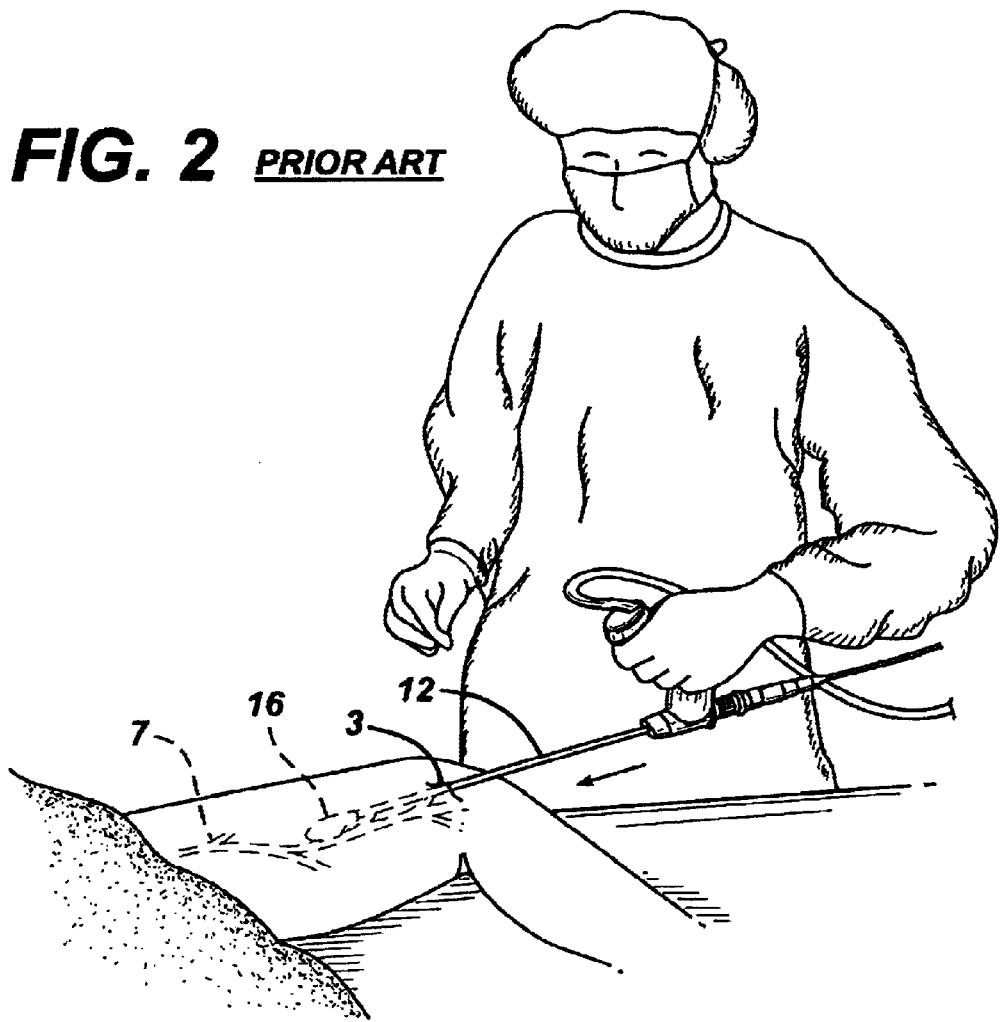
FIG. 2 illustrates a perspective view of a surgeon and an endoscopic vessel harvesting device of the prior art harvesting a vein located in a persons leg.
Figure 3:
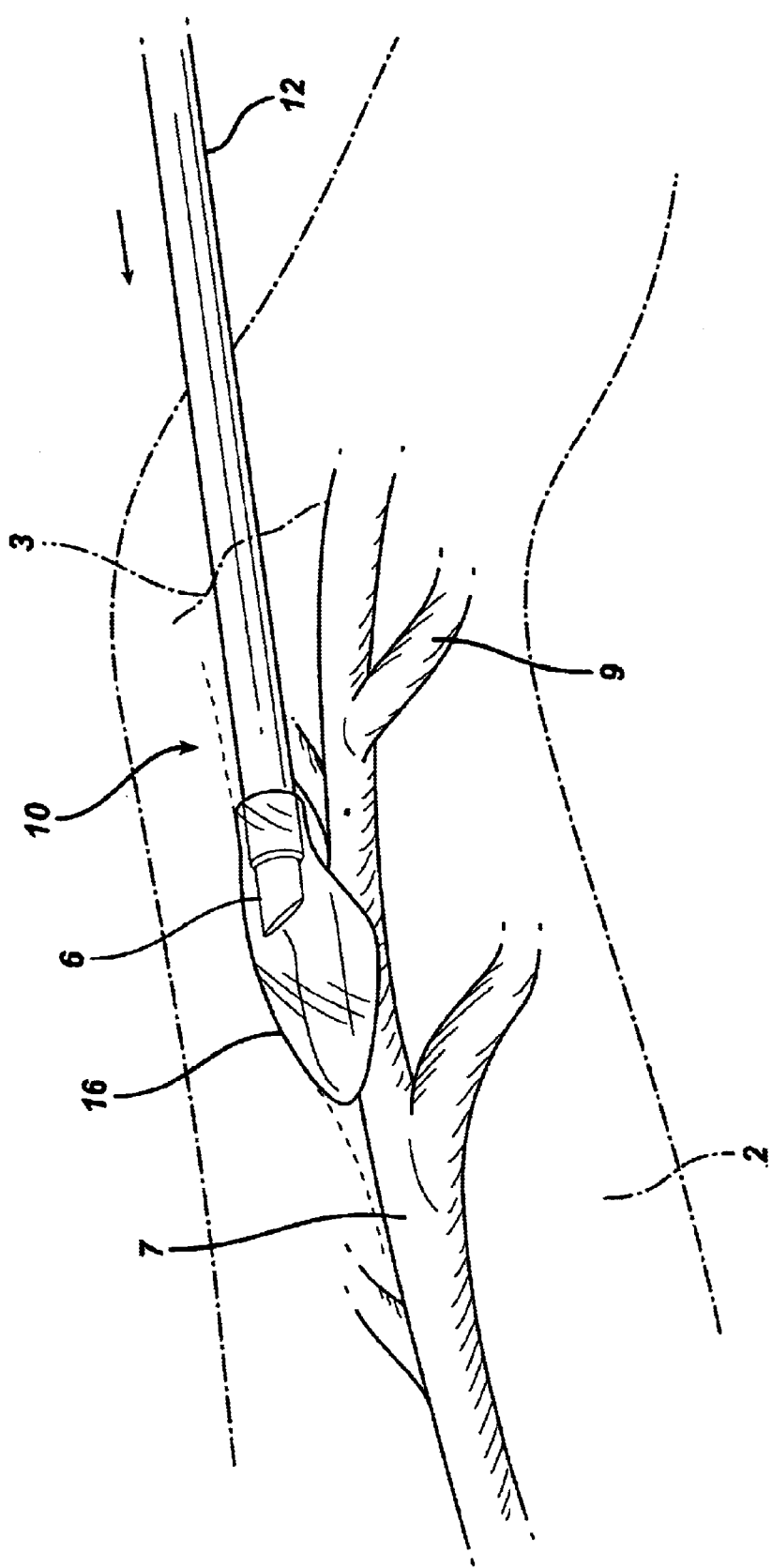
FIG. 3 illustrates an enlarged perspective view of the endoscopic vessel harvesting of FIG. 1 inserted into a patient during a procedure to harvest a vein.

Traditionally, as shown in FIGS. 1–3 blunt dissection of the saphenous vein is performed on the anterior or upper side of the vessel upon insertion of a vessel harvesting device. Upon dissection above the vessel a work space is created allowing further tools to be inserted into the patient so that the vessel can be further dissected, any side branch vessels can be ligated and transected and the vessel can be removed. In the traditional system, the dissection of the vessels from tissues on the posterior or under side of the vessels is performed using a variety of devices and can be a time consuming procedure requiring a great deal of skill to perform.

The present invention greatly reduces the number of tools required to perform this very same task and provides an easier method for the removal of a vein from the patient.

Figure 4:
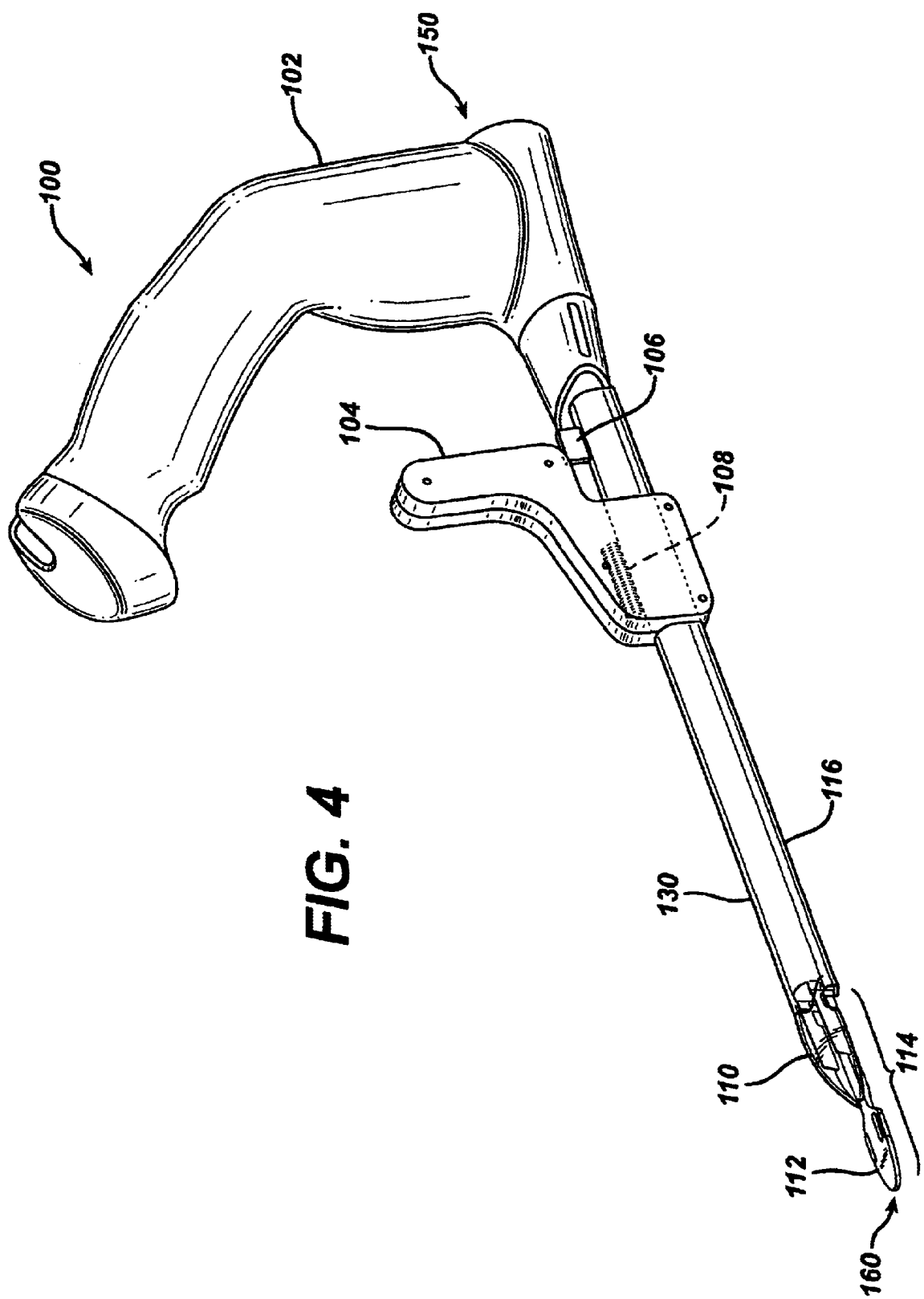
FIG. 4 illustrates a perspective view of a preferred implementation of an endoscopic vessel harvesting device of the present invention.

Referring now to FIG. 4, there is illustrated a preferred implementation of an endoscopic vessel harvesting device (EVH) for the removal of blood vessels from a patient, generally referred to by the reference number 100. Specifically this EVH device 100 is often used for the removal of the saphenous vein from the leg of a person undergoing a CABG procedure. The embodiments discussed herein are directed to the removal of such a vein however, the removal of the saphenous vein is only used by way of example only and not to limit the scope and spirit of the present invention. The EVH 100 can be utilized for the removal of a number of vessels from a patient, including the radial artery of the lower arm, the lesser saphenous vein in the leg, and the interior epigastric artery in the abdomen.

The EVH 100 device includes, a headpiece 114 situated on the distal end 160 of a hollow shaft 116. The hollow shaft 116 is preferably a medical grade metal such as stainless steel. The headpiece 114 is used for blunt vessel dissection, which is the separating of tissues connected to the vessel.

The headpiece 114 comprises a top portion 110 and a bottom portion 112. The headpiece 114 may be made of a medical grade transparent plastic such as a polycarbonate. The top and bottom portions completely surround a vessel which is inserted into the device. The top portion 110 has an entry hole 132 (shown more clearly in FIG. 7) on the leading edge of the headpiece 114. The entry hole 132 provides a path for the vessel to enter the headpiece 114. The headpiece 114 also has holes 126 (also shown more clearly in FIG. 7) for the exiting of the vessel from the headpiece 114 after it has been dissected. The entry and exit holes 132 and 126 are shown by way of example on the top and bottom portion 110 and 112, respectively. However, the location of the entry and exit holes can be switched or both can be on one portion.

Figure 6:
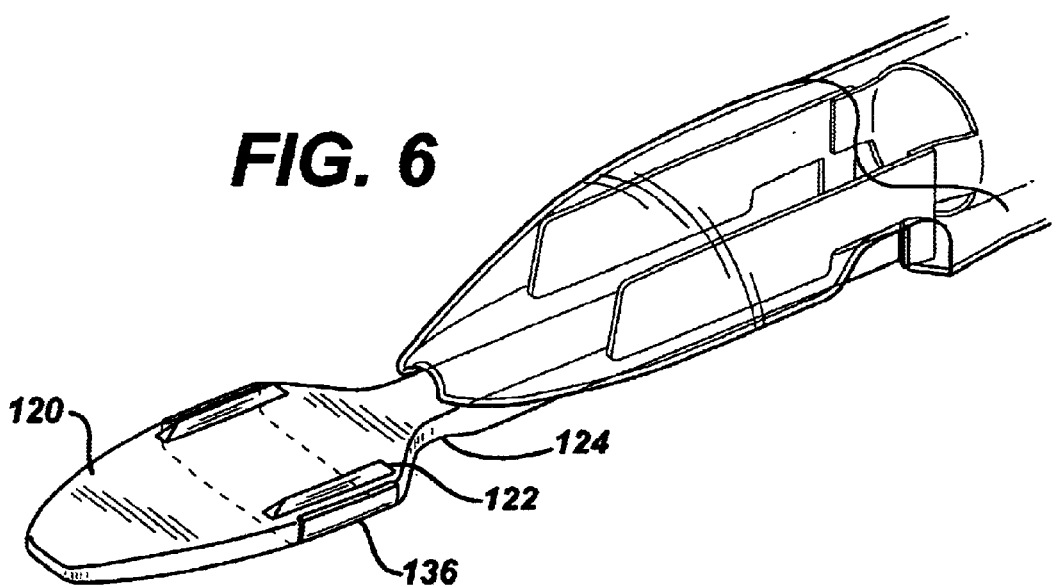
FIG. 6 illustrates an enlarged view of the two portion headpiece of the endoscopic harvesting device of FIG. 4 in which the bottom portion is extended.
Figure 7:
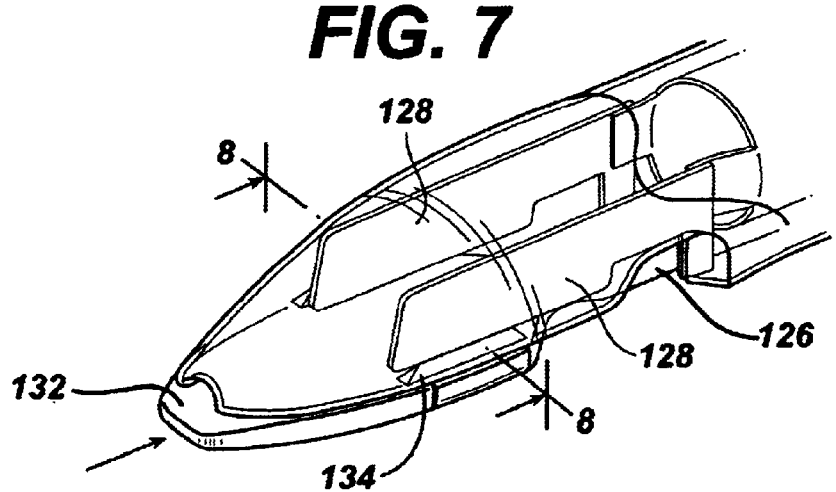
FIG. 7 illustrates an enlarged view of the two portion headpiece of the endoscopic harvesting device of FIG. 4 in which the bottom portion is partially retracted.
Figure 8:
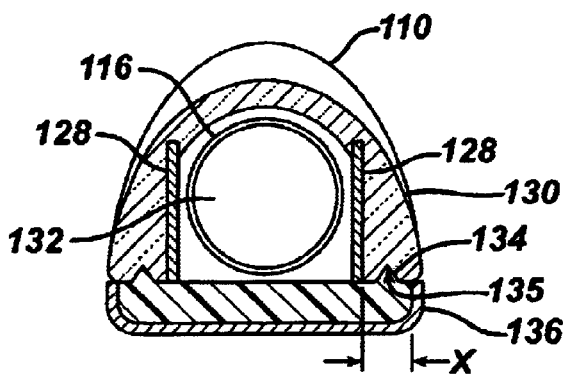
FIG. 8 illustrates cross sectional view of a two portion headpiece for the endoscopic harvesting device of FIG. 7, taken along line 8—8.

As shown in FIG. 6, bi-polar ligation electrodes 136 and 128 are preferably affixed inside of the headpiece 114 for ligating side branch vessels. The location of the electrodes 136, 128 in the headpiece 114 allows the user of the device to ligate side branch vessels upon their discovery without the insertion of other tools. This increases the efficiency of the overall process. FIGS. 6–8 show the relationship of the electrodes 128 and 136 to each other and other features of the headpiece 116. Electrodes 128 are attached to the shaft 116 of the device, these may be either manufactured as part of the shaft 116, or they may be separately made and affixed, by welding for example. Electrodes 136 are located on the bottom portion 112 of the headpiece 114. However, as shown in FIG. 8, the electrodes 136 and 128 are not located in the same vertical plane but rather are off-set from one another, by an off-set distance of X the offset distance has been determined to be in the range of approximately 1–3 mm and preferably 2 mm. This position insures that the electrodes cannot touch as this would result in a shorted circuit. FIGS. 6 and 7 show two pairs of electrodes, each off-set to a side of the headpiece 114. By having two sets of electrodes 128 and 136 the device is capable of ligating side branch vessels on either side of the saphenous vein.

Figure 9:
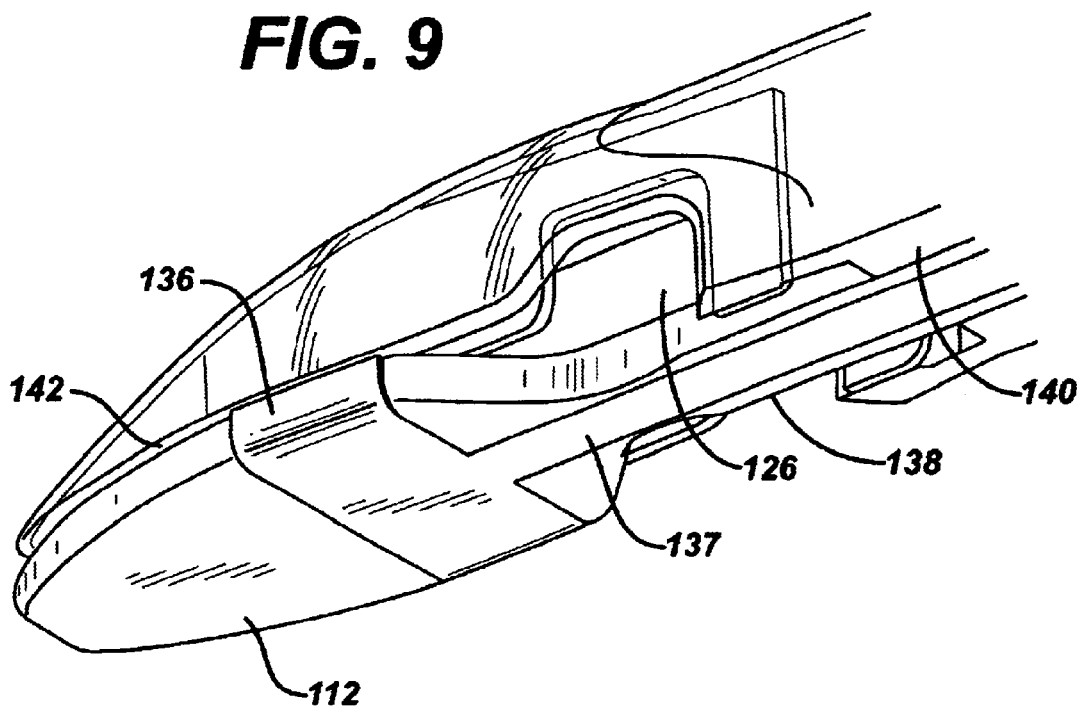
FIG. 9 illustrates a lower perspective view of the two portion headpiece f the endoscopic vessel harvesting device of FIG. 4.
Figure 10:
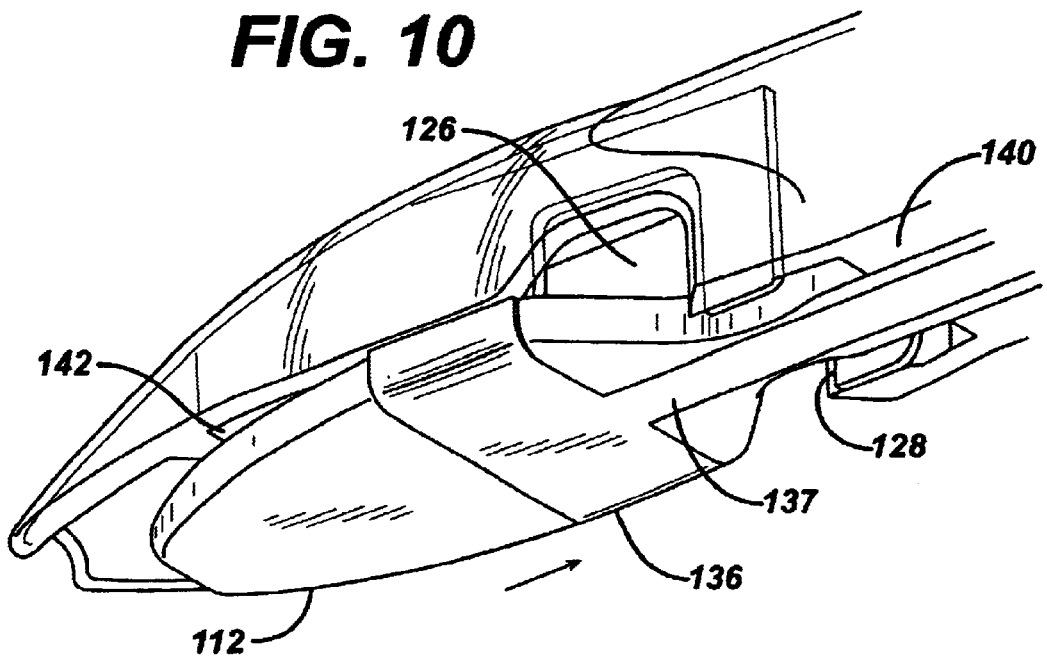
FIG. 10 illustrates a lower perspective view of the two portion headpiece of the endoscopic vessel harvesting device of FIG. 4 in which the lower portion is fully retracted.

The electrodes 136, 128 are preferably comprised of a positive and a negative terminal. One being located in the top portion and the second located in the bottom portion of the headpiece. They may be constantly energized or may be energized at will by the user. The triggering means is located either in the handle 103 of the device, or in a foot pedal (not shown). The electrodes are connected to a conventional bi-polar RF generating device. FIG. 9 shows the slide 138 having an electrically conductive portion 137. This electrically conductive portion 137 connects to the lower electrodes 136 of the ligation means. The upper electrodes 128 are connected to the shaft 116. The shaft 116 is connected to the RF energy generating means as is known in the art. Additionally, in this configuration, the conductive portion 137 of the slide 138 is insulated with an insulative coating to prevent inadvertent discharge of energy to surrounding tissue. Suitable insulative coatings are well known in the art, such as parylene-n.

Upon entry of a side branch vessel between the two electrodes 128, 136 the vessel is compressed by the proximity of the top and bottom portions 110, 112 of the headpiece 114. The vessel is then coagulated by the energized electrodes 128,136. The coagulation results in effective ligation of the side branch vessel. Because the coagulation zone is limited to the small distance X, approximately 1–3 mm, the RF energy does not spread to the harvested vessel. These ligated sections may then be transected, freeing the saphenous vein from the side branch vessels. As shown in FIGS. 6–8 the transection means is preferably sharply raised cutting sections 134 located on the bottom portion 112 between the electrodes 128 and 136. The cutting section 134 transects the ligated vessel as the lower portion 112 is articulated back and forth over the side branch vessel. The cutting section 134 also creates a high spot in the bottom portion 112. This high spot assists in the compression of the side branch vessel for coagulation and ligation. The cutting section 134 aligns with a cutting groove 135 in the top portion 110 to align the upper and lower portions of the headpiece 114 (as shown in FIG. 8), and to hold concentrate the compression at a tip of the cutting element 134 for dividing tissue when lower portion 112 is moved reciprocally relative to the upper portion 110. Additionally, the lower portion 112 is springably held against the upper portion 110 so that various thickness of vessels may be captured in a compression zone between the cutting element and the cutting groove 135.

Because the transection means 134 is fabricated from hard plastic the transection of vessels can be perform without the introduction of sharp metallic cutting instruments into the incision. This greatly reduces the chances of accidental injury in the surgical site. Further, because the compression zone X is a sliding compression zone, and is used in combination with RF energizing of the electrodes 128, 136, ligation of the vessels can be done hemostatically. This is particularly assisted by a high compression zone formed at the tip of the cutting means 134 which allows the coagulation to occur simultaneously with the cutting of the vessel.

Referring now to FIG. 4, the shaft 116 may be inserted into a molded sheath of plastic 130. This sheath of plastic 130 extends the length of the shaft and may incorporate the upper portion 110 of the headpiece 114. This allows for single component construction of a large section of the EVH 100. The molded sheath 130 also comprises an affixing means which connects the sheath 130 to the handle 102. On the upper surface of the molded sheath is preferably a stop 106 which is used in connection with an actuation means 104. On the underside of the molded sheath is a track 140. Track 140 allows for the insertion of a slide 138 which can be connected to the actuator 104 of the articulation means. The track 140 may be constructed so that when viewed in the cross section the opening is smaller than the width of the slide 138. This configuration insures that the slide 138 cannot fall out of the track 140. The bottom portion 112 may be connected to the slide 138 and a handle of an articulating means 104 of the EVH 100. The articulating means allows the bottom portion 112 to move independently of the top portion 110. Alternatively, the molded sheath 130 could separate from the headpiece 114. In that instance, the top portion 110 may be rigidly affixed to the shaft 116 of an EVH 100.

One method of articulation of the bottom portion 112 is to attach an actuator 104 connected to a slide 138 the slide 138 in turn connects to the bottom portion 112 of the headpiece 114. The slide 138 runs in a track 140 located on the underside of the EVH 100. In practice, the actuator 104 provides the actuation means and the slide 138 allows for the translation of force from the actuator 104 to the bottom portion 112 of the headpiece 114. In the device shown in FIG. 4, the actuator 104 is biased in the distal direction 160 by a spring 108, which is forced against a stop 106. By squeezing the actuator 104 the bottom portion 112 is moved towards the proximal end 150 of the EVH 100. Upon release of pressure on the actuator 104 the stored spring force moves the bottom portion 112 towards the distal end 160 of the EVH 100. Another feature of the slide 138 is that it may be constructed at least partially of an electrically conductive material. In the preferred implementation the slide 138 supplies RF energy to the electrode 136.

The actuation of the articulation means may be manually performed or it may be motorized. In the device shown in FIGS. 4 and 5, the device is manually articulated. The articulation means may provide for variable stroke or longitudinal translation pf the lower portion 112 with respect to the upper portion 110, preferably in the range of 0.1 mm to 5 mm, for either manual or motorized actuation means. The rate of articulation may also be variable. Those skilled in the art can appreciate that a relatively high rate, such as 10 reciprocations/sec with a small stroke such as 0.2 mm may be provided via a motorized means, and variably controlled by the operator.

Figure 5:
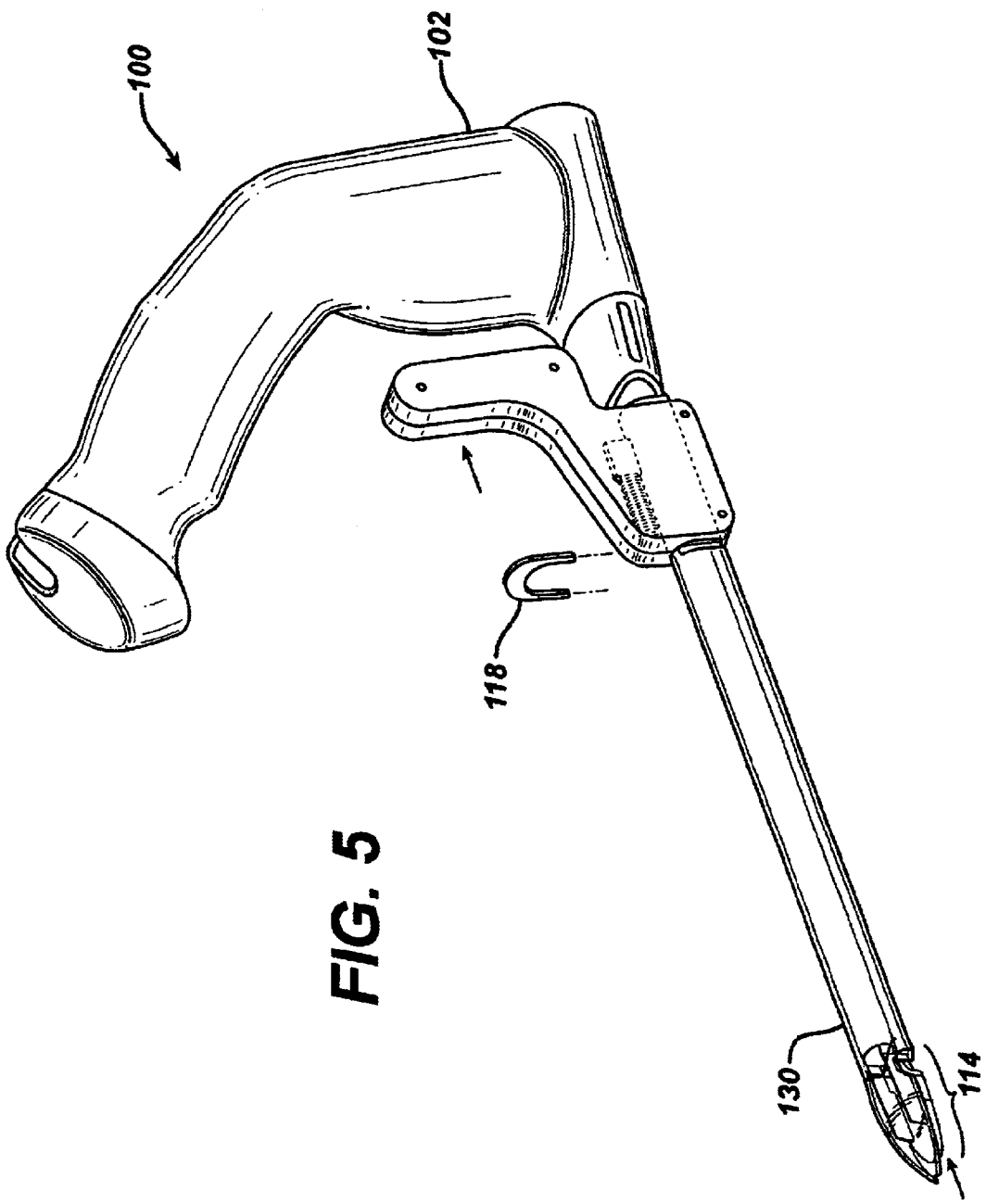
FIG. 5 illustrates a perspective view of the endoscopic vessel harvesting device of FIG. 4 having the bottom portion of the headpiece retracted.

Additionally, in FIG. 5 there is shown a preventing means 118 for preventing the articulated portion of headpiece 114 from moving. This is preferably accomplished by preventing the articulating means from functioning. In the case shown in FIG. 5, the handle 104 is prevented from moving towards the distal end 160 of the device by the preventing means 118, this in turn prevents the bottom portion 112 from moving in the same distal direction 160. In the preferred embodiment, as shown in FIG. 5, the Preventing means 118 is a U-shaped clip which attaches to the molded sheath 130 in cooperation with a slot in the molded sheath 130. Alternatively, the preventing means can be any means which prevents the spring 108 from acting on the handle 104 and moving the bottom portion 112 in the distal direction 160.

In the device described above, the bottom portion 112 can be projected under the saphenous vein in a reciprocating fashion while the upper portion 110 is forced over the saphenus vein. This results in the effective dissection of both the upper and lower sides of the vessel without the use of extra tools. However, before this can occur the vessel must be inserted into the device.

Insertion of the vessel is performed by extending the bottom portion 112 of the headpiece 114 in a manner as shown in FIG. 6. In the configuration, a pre-dissected portion of the vessel can be inserted into the headpiece 114. The extended bottom portion 112 is positioned under the vessel and the top portion 110 is drawn over the top of the vessel. By placing the vessel over the bottom portion 112 in the extended state, a proximate portion of the vessel is allowed to sit in a notch 124 of the bottom portion 112. When the top portion 110 is drawn over the lower portion that section of the vessel which was formerly located in notch 124 will then be positioned in the exit opening 126. As the top portion is drawn forward, a distal portion of the vessel is positioned in the entry hole 132. At this point the device is in position to begin operation.

Although the headpiece 114 is shown and discussed as an integral portion of the EVH 100, alternatively it can be separately provided to fit onto existing vessel harvesting instruments.

The dissection of the saphenous vein from the surrounding tissue is done in an efficient and expedient manner and requires a limited number of tools and with a minimum number of tool exchanges using the EVH 100 described above.

The present method starts as is common for endoscopic vessel harvesting by locating the vessel which is to be removed. Next an incision is made to accommodate the insertion of the EVH 100. Upon insertion of the leading edge of the EVH 100 blunt dissection of the tissue on the anterior or upper side of the vessel is performed.

Next, pre-dissection of a section of the vessel is performed. This pre-dissection is performed so that a portion of the vessel can be fully exposed, of particular interest is the tissue located on the posterior or underside of the vessel. The pre-dissection can be performed using the EVH 100, or with the use of specialized tools such as those known in the art. Upon full exposure the vessel can be inserted into the headpiece 114 of the EVH 100. This insertion is performed as discussed above. Once inserted into the EVH 100 the vessel's dissection from the surrounding tissue is continued by the movement of one of the top and bottom portions being thrust in the direction of the distal end 160 of the device. This movement is independent of the other of the top and bottom portions. One variation of dissection could be to alternate the movement of the top and bottom section so that dissection only occurs on one surface of the vessel at a time. A second variation of use of the EVH 100 would be to repeatedly compress the handle 104 and release it. This causes the lower portion 112 of the headpiece 114 to continually dissect a short section of the underside of the saphenous vein. This repeated compression is performed while the upper portion 110 of the headpiece 114 is continually advanced along the upper side of the saphenous vein to dissect that surface. In either variation the actuation of the device is continued, dissecting above and below the vessel until sufficient length of the vessel is dissected.

The ability to dissect both above and below the vessel using only a single tool results in greater efficiency for the user by minimizing the tool exchanges and a shorter time period for the procedure by simplifying the method of dissecting below the vessel.

The saphenous vein will invariably be connected to a series of side branch vessels. In order to remove the saphenous vein for further use these side branch vessels must be individually ligated and transected. As discussed above, the EVH device is equipped with bi-polar electrodes 128, 136 located in the headpiece 114. These electrodes are triggered by the user upon the placement of a side branch vessel between the two electrodes. These electrodes effectively ligate the side branch vessels and allow them to be transected. In the present invention, this is performed during the dissection of the vessel. For example, the lower portion 112 of the headpiece 114 dissects below the vessel and uncovers a side branch vessel. Upon the movement of the upper portion to meet the lower portion, the side branch vessel will be forced between the electrodes 128 and 136. One electrode 128 being on the bottom portion 112 and the other electrode 136 being housed in the upper portion 110 of the headpiece 114. As the upper portion 110 is slid over the bottom portion 112 the side branch vessel is compressed between the two electrodes 128 and 136 and the cutting means 134. The user then triggers the bi-polar electrodes either 128 or 136 and the side branch vessel is ligated. The side branch vessel is transected using the cutting means 134 by the reciprocating motion of the bottom portion 112. In an alternative use the operator may energize RF energy continuously while advancing the headpiece 114 of the device along the vessel, while maintaining visualization of the vessel and the side branches within the working space.

After sufficient length of the saphenous vein is dissected and the side branch vessels are ligated, the saphenous vein itself is ligated on both the distal and proximate ends. Once this is performed and the vessel is not attached to any of the other surrounding tissue it can be removed and used in further procedures, such as CABG.

Although only a few exemplary embodiments of this invention have been described in detail above, those skilled in the art will readily appreciate that many modifications are possible without materially departing from the novel teachings and advantages of this invention. Accordingly, all such modification is intended to be included within the scope of this invention as defined in the following claims.

What is claimed is:

1. A vessel harvesting device comprising:
   a shaft having a lumen for insertion of an endoscope there through;
   a handle located on a proximal end of the shaft for allowing an operator to manipulate the device;
   a headpiece connected to a distal end of the shaft, the headpiece having top and bottom portions defining a gap to surround a vessel inserted therein, and for dissecting the vessel from the surrounding tissue, the headpiece having a first opening for receiving a dissected portion of the vessel and one or more second openings for allowing the dissected portion of the vessel to exit the headpiece; wherein the endoscope facilitates visualization of a workspace defined by the headpiece;
   an actuator for reciprocating one of the top and bottom portions relative to the other of the top and bottom portions, wherein the vessel is dissected from the surrounding tissue by reciprocating one of the top portion and the bottom portions as the headpiece is advanced along the length of the vessel.

2. The vessel harvesting device as recited in claim 1, further comprising:
   ligation means and transection means for ligating and transecting side branch vessels, respectively.

3. The vessel harvesting device as recited in claim 2, wherein the ligation means comprises a least one pair of bi-polar electrodes, each electrode being of a different polarity.

4. The vessel harvesting device recited in claim 3, wherein the at least one pair of bi-polar electrodes comprises two pairs of electrodes one of said pairs of electrodes being offset to a first side from a centerline of the device and the second of said pairs of electrodes being offset to a second side from the centerline of the device.

5. The vessel harvesting device as recited in claim 3, comprising energizing means for energizing the bi-polar electrodes with RF energy.

6. The vessel harvesting device as recited in claim 1, wherein the actuating means includes a preventing means for preventing one of the top and bottom portions from articulating relative to the other.

7. The vessel harvesting device of claim 2, wherein the transection means comprises at least one raised cutting means located on the one of the top and bottom portions of the headpiece which is reciprocated relative to the other, wherein the transection is caused by the reciprocation of the cutting means across a side branch vessel.

8. The vessel harvesting device of claim 1, wherein the bottom portion is biased against the top portion for compression of tissue in a compression zone for automatically accommodating vessels of various thickness.

9. A headpiece for an endoscopic vessel harvesting device comprising:

a top portion for dissecting the tissue above a vessel which is to be removed, the top portion being rigidly attached to the endoscopic harvesting device;

a bottom portion for dissecting the tissue below the vessel to be removed, the bottom portion being connected to the endoscopic harvesting device by an articulated connection, the top and bottom portions defining a gap to surround the vessel;

a first opening allowing a dissected portion of the vessel to enter the headpiece;

one or more second openings allowing a dissected portion of the vessel to exit the headpiece after dissection, wherein a vessel is dissected from its surrounding tissue by reciprocating the bottom portion relative to the top portion while traversing the length of the vessel.

10. The headpiece for an endoscopic vessel harvesting device as recited in claim 9, further comprising ligation means and transection means for ligating and transecting side branch vessels.

11. The headpiece for an endoscopic vessel harvesting device as recited in claim 10, wherein the ligation means comprises a least one pair of bi-polar electrodes, each electrode being of a different polarity.

12. The headpiece for an endoscopic vessel harvesting device as recited in claim 11, wherein the at least one pair of bi-polar electrodes comprises two pairs of electrodes one of said pairs of electrodes being offset to a first side from a centerline of the device and the second of said pairs of electrodes being offset to a second side from the centerline of the device.

13. The headpiece for an endoscopic vessel harvesting device as recited in claim 11, comprising energizing means for energizing the bi-polar electrodes with RF energy.

14. The headpiece for an endoscopic vessel harvesting device as recited in claim 9, wherein the transection means comprises at least one raised cutting means located on the bottom portion of the headpiece which is reciprocated relative to the top portion, wherein the transection is caused by the reciprocation of the cutting means across a side branch vessel.

15. A method of vessel dissection comprising the steps of;

(a) locating the vessel to be harvested;

(b) making an incision to expose the vessel;

(c) pre-dissecting the vessel from tissue above the vessel;

(d) pre-dissecting the vessel from the tissue below the vessel;

(e) inserting a portion of the vessel which has been pre-dissected into a two piece headpiece of a vessel harvesting device so that a top and a bottom portion of the headpiece surround the vessel;

(f) dissecting the tissue above the vessel using the top portion of the headpiece by projecting the top portion of the headpiece along the vessel;

(g) simultaneously, dissecting the tissue below the vessel by reciprocating the bottom portion to of the headpiece;

(h) traversing the length of the vessel while repeating steps (f) and (g), wherein the reciprocating dissection both above and below the vessel reduces the stress on the vessel and prevents the vessel from being prematurely severed;

(i) ligating and transecting the dissected vessel; and (j) removing the vessel.

16. The method as described in claim 15, wherein the traversing step further comprises the step of ligating and transecting side branch vessels of the vessel.

17. The method as described in claim 16, wherein the ligation and transection of the side branch vessels further comprises the step of energizing a bi-polar electrode ligation means to ligate side branch vessels.

18. The method as described in claim 15, wherein the ligation and transection of the side branch vessels further comprises the step of cutting the side branch vessels by repeatedly drawing a raised cutting means housed on a lower portion of a headpiece across a side branch vessel.

19. A method of transecting a vessel, the method comprising:

providing a vessel harvesting device including compression means, the compression means defining a slidable compression zone and formed of a cutting element and a cutting groove, the compression means further defining a compression zone having concentrated compression for coagulating a vessel captured by the vessel harvesting device; electrodes for ligation of the captured vessel; and a transection means;

compressing a vessel in the slidable compression zone between the cutting element and the cutting groove;

energizing the electrodes with RF energy to simultaneously cauterize the vessel being compressed; and cutting the vessel being compressed by reciprocation of the cutting element in the cutting groove with the vessel compressed therein, wherein the simultaneous compression, cauterization, and cutting hemostatically divides the vessel.

\* \* \* \* \*

UNITED STATES PATENT AND TRADEMARK OFFICE
Certificate

Patent No. 6,740,102 B2　　　　　　　　　　　　　　　　　　　　　　　　Patented: May 25, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christopher J. Hess, Lebanon, OH; Michael Clem, Maineville, OH; Gary W. Knight, West Chester, OH; Kristin L. Jambor, Cincinnati, OH; Gary L. Long, Mariemont, OH; Dale R. Schulze, Lebanon, OH; and Rudolph H. Nobis, Mason, OH.

Signed and Sealed this Ninth Day of November 2004.

*Anhtuan T. Nguyen*
*Supervisory Patent Examiner*
*Art Unit 3731*